United States Patent [19]

Strong

[11] Patent Number: 4,641,250
[45] Date of Patent: Feb. 3, 1987

[54] INSPECTION WORKSTATION DATA ENTRY METHOD

[75] Inventor: David Strong, Millersville, Md.

[73] Assignee: The United States of America as represented by the Secretary of the Air Force, Washington, D.C.

[21] Appl. No.: 619,244

[22] Filed: Jun. 11, 1984

[51] Int. Cl.⁴ .................. G06F 15/46; G06F 11/30
[52] U.S. Cl. ............................. 364/507; 364/481; 371/25
[58] Field of Search .......... 364/480, 481, 491, 506, 364/507, 550, 551; 371/25, 26

[56] References Cited

U.S. PATENT DOCUMENTS

| | | | |
|---|---|---|---|
| 3,828,306 | 8/1974 | Angeloni | 340/286 M |
| 4,005,281 | 1/1977 | Faulhaber et al. | 364/507 |
| 4,022,969 | 5/1977 | McKinlay et al. | 178/18 |
| 4,222,036 | 9/1980 | Troukens | 340/286 M |
| 4,313,109 | 1/1982 | Funk et al. | 340/365 P |
| 4,454,585 | 6/1984 | Ele | 364/507 |
| 4,484,081 | 11/1984 | Cornyn, Jr. et al. | 364/507 X |
| 4,484,329 | 11/1984 | Slamka et al. | 371/25 |

Primary Examiner—Felix D. Gruber
Attorney, Agent, or Firm—Stanton E. Collier; Donald J. Singer

[57] ABSTRACT

An inspection workstation data entry method is used by electronic assembly inspector to substantially increase throughput and eliminate data entry errors. The method utilizes a sonic digitizer cursor and x-y linear microphones to record unique registration data and defect data. The inspector, without manual intervention for data entry, positions the assembly in a workarea, records a registration hole location and defect locations along with identifying information or processing requirements. The method minimizes errors due to manual data entry and eliminates the need for on-hand reference materials.

3 Claims, 8 Drawing Figures

FIG.4
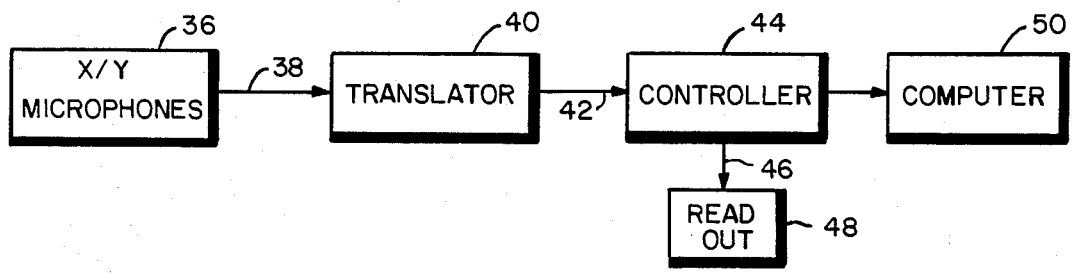
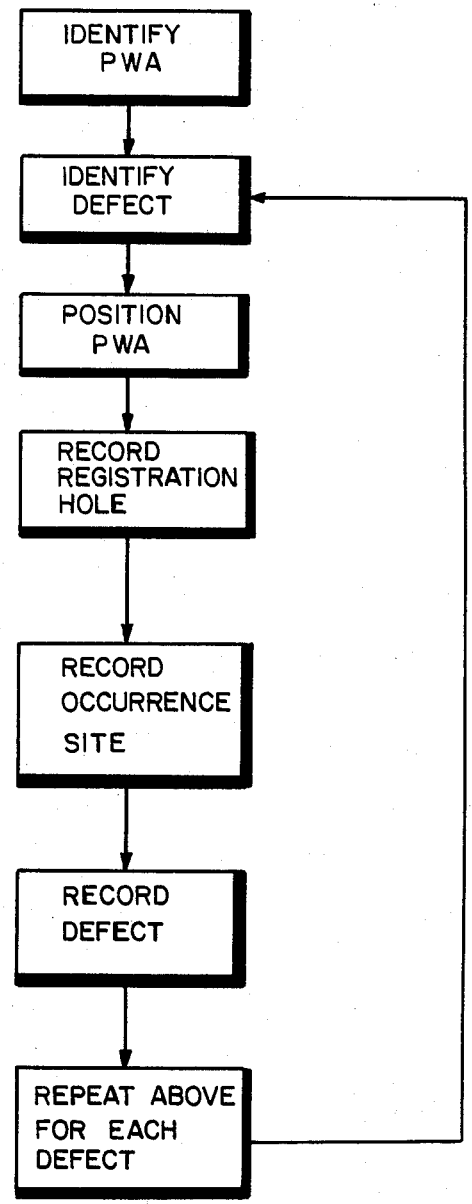
FIG.5

| ASSEMBLY NO. | 9 | 1 | 8 | 1 | 9 | 4 | 3 | |
|---|---|---|---|---|---|---|---|---|
| PART TYPE | R | E | S | | | | | |
| PART NO. | 4 | 2 | | | | | | |
| DEFECT | D | A | M | A | G | E | | |

INSPECTION WORKSTATION DATA ENTRY METHOD

STATEMENT OF GOVERNMENT INTEREST

The invention described herein may be manufactured and used by or for the Government for governmental purposes without the payment of any royalty thereon.

BACKGROUND OF THE INVENTION

The present invention relates to a method of achieving high productivity improvement in automated manufacturing, and, in particular, relates to a method of increasing greatly an inspection workstation's throughput and data accuracy as related to items inspected.

Presently items such as printed wiring assemblies (PWA) having components thereon can be produced in an automated manner in great numbers. Although one would expect perfection in such a process, many defects do, indeed, occur to the dismay of all concerned. In order to reduce these defects of whatever nature, quality control personnel must first identify the defect. Obviously, if these boards are created in the thousands, or even in greater number, the inspection of each board becomes an almost inhuman task. In some places, boards can be randomly inspected or inspected at given intervals, such as every 10th or 100th board. An electronic tester may be used to identify a detective board, but a visual inspection may still be required if the defect is not in an identifiable component. Although this may not always be the case, every defective board may still be examined visually to determine the sources of error, if a visual one.

An inspector under the above conditions would identify the visual defect. This requires that he have volumes of reference material at hand to properly identify parts, etc. Once properly identified, this information must be manually recorded or perhaps even entered into a CRT type of terminal by hand by the inspector. This is very tedious taks, slows the throughput, and is even subject to error by the inspector himself thus compounding a quality control problem that once only existed on the board. If this information is manually recorded, it must further be typed onto computer cards or entered into a CRT type of terminal by a data entry clerk.

Obviously the chance for error in the above process is substantial. Further, the inspector is slowed in the process since he must use numerous references and record vast quantities of information.

These drawbacks have motivated a search for a method that minimizes the chance for error and further allows the inspector to substantially increase the number of items inspected per unit of time, the throughput rate.

SUMMARY OF THE INVENTION

The present invention set forth a method and apparatus for recording defects in printed wiring assemblies (PWA).

A PWA requiring inspection is placed against a reference bar that is positioned on a flat working area such as a table. This area has positioned thereon in an orthogonal manner a linear x-axis microphone and a linear y-axis microphone. The reference bar being parallel to the x-axis microphone.

The working area exists between the x-axis microphone, the bar and the y-axis microphone so that a PWA can be placed against the bar.

After the PWA is positioned against the bar, a hand-held sonic digitizer cursor is positioned over a unique registration hole in the PWA and activated. The sound from the cursor is picked up by the linear orthogonal microphones and is translated into x-y coordinates. This action locates the PWA within the working area and provides a measurement reference point for subsequent actions.

The PWA is identified by the inspector before starting the actual inspection process. This can be done by a bar code placed on the PWA and then read by a bar code reader or can be entered by keyboard associated with a local CRT terminal.

After this, the cursor is then placed over the identified defect and again activated. This identifies the location of the defect. Next, the cursor is placed over a menu, a flat picture having defect identifier blocks thereon, and again the cursor is activated. This sequence is repeated for each deviation on the PWA. A local controller having the needed references stored would output to the inspector relevant data as to each PWA inspected.

It is therefore one object of the present invention to provide for an inspection workstation data entry method that automatically records information relevant to deviations on printed wiring assemblies.

It is therefore another object of the present invention to provide for an inspection workstation data entry method wherein an inspector need not reference material or manually enter data.

It is another object of the present invention to provide for an inspection workstation data entry method that substantially increases the number of items inspected per unit of time.

These and many other objects and advantages of the present invention will be readily apparent to one skilled in the pertinent art from the following detailed description of a preferred embodiment of the invention and the related drawings.

BRIEF DESCRIPTION OF THE DRAWINGS

FIG. 4 is a functional block diagram of the electronics necessary to operate the inspection workstation of the present invention.

FIG. 5 illustrates by flow chart the steps the inspector follows in using the inspecting workstation of the present invention;

DETAILED DESCRIPTION OF THE PREFERRED EMBODIMENT

The need to accurately and expeditiously identify and document electronic assembly manufacturing process defects and provide a timely feedback for process control has grown in significance to the point that it is a prime limiting factor in achieving productivity improvements in automated manufacturing. The information used to assess product quality and the effectiveness of automated manufacturing process originates at the inspection workstation. To be compatible with automated assembly, a means of increasing the inspection workstation data accuracy and throughput must be provided. The inspector's daily throughput is directly dependent on the number of items to be evaluated per unit time, accept/reject criteria and the frequency of defect occurrence requiring accounting and documentation.

Figure 1:
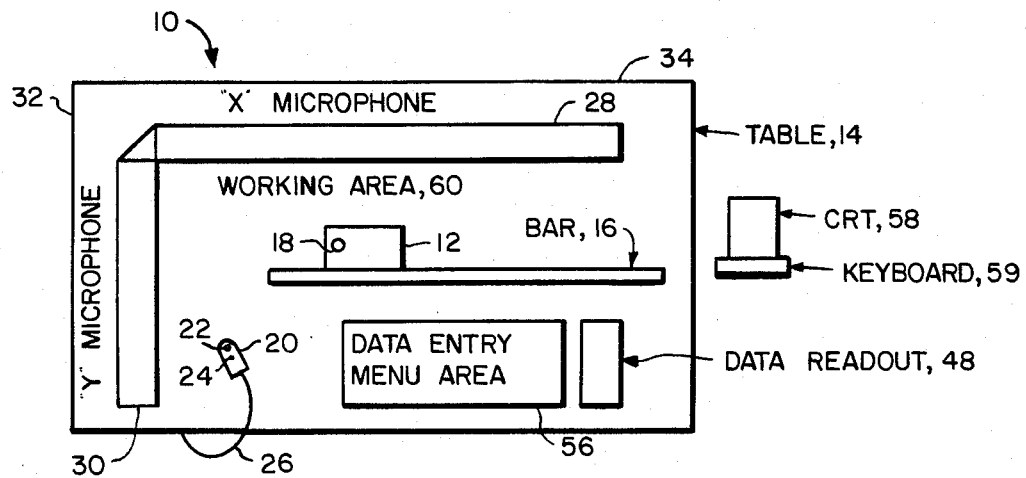
FIG. 1 is a plan view of an inspection workstation of the present invention.

Referring to FIG. 1, an inspection workstation 10 is shown for processing electronic components such as conventional printed wiring assemblies (PWA) 12.

The inspector before starting the defect identifying procedure must identify each PWA 12 to be examined. This can be accomplished by entering identifying information into a keyboard 59 associated with a CRT display 58 or by use of a bar code attached to each PWA 12 and read by a bar code reader, not shown.

After initializing information is entered, such as noted above, the inspector places PWA 12 upon a table 14 in a working area 60 and against a reference bar 16 as seen in FIG. 1.

Reference bar 16 acts as a curb upon which PWA 12 is positioned. Reference bar 16 also prevents PWA 12 from slipping if table 14 is positioned at an angle for ease of work.

Figure 2:
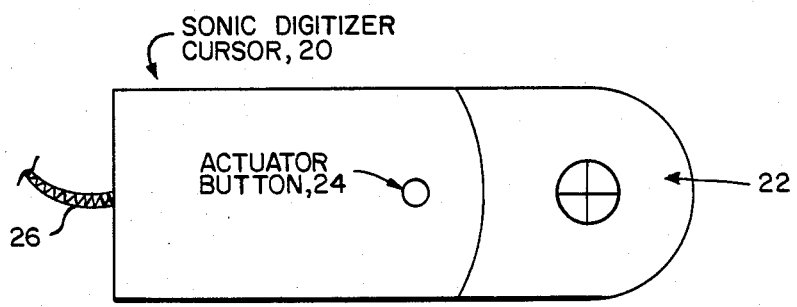
FIG. 2 is a view of the sonic digitizer cursor used in the present invention.

Each time PWA 12 is placed on working area 60 by the inspector, its position thereon must be determined in the x-y plane. Each PWA 12 has a single registration hole 18 therethrough for that purpose. Once the PWA 12 is positioned against reference bar 16, the inspector takes the hand-held sonic digitizer cursor 20, FIG. 2, and centers a reticle 22 over the registration hole 18. Once centered, an actuator button 24 on cursor 20 is depressed. This causes an ultrasonic sound to be emitted from the centered cursor 20. The sound emitted is detected by a linear x-microphone 28 and a linear y-microphone 30 located at a side 32 and a top 34 of table 14. These microphones 28 and 30 provide signals that are used to determine the x-y location of the registration hole 18.

Once the position of the PWA 12 is determined, the inspector will then place and center cursor 20 over a visual defect. The actuator button 24 is then depressed which causes the x-y location of this defect to be loaded into the computer 50 and associated with the PWA 12 that was last identified.

Figure 3:
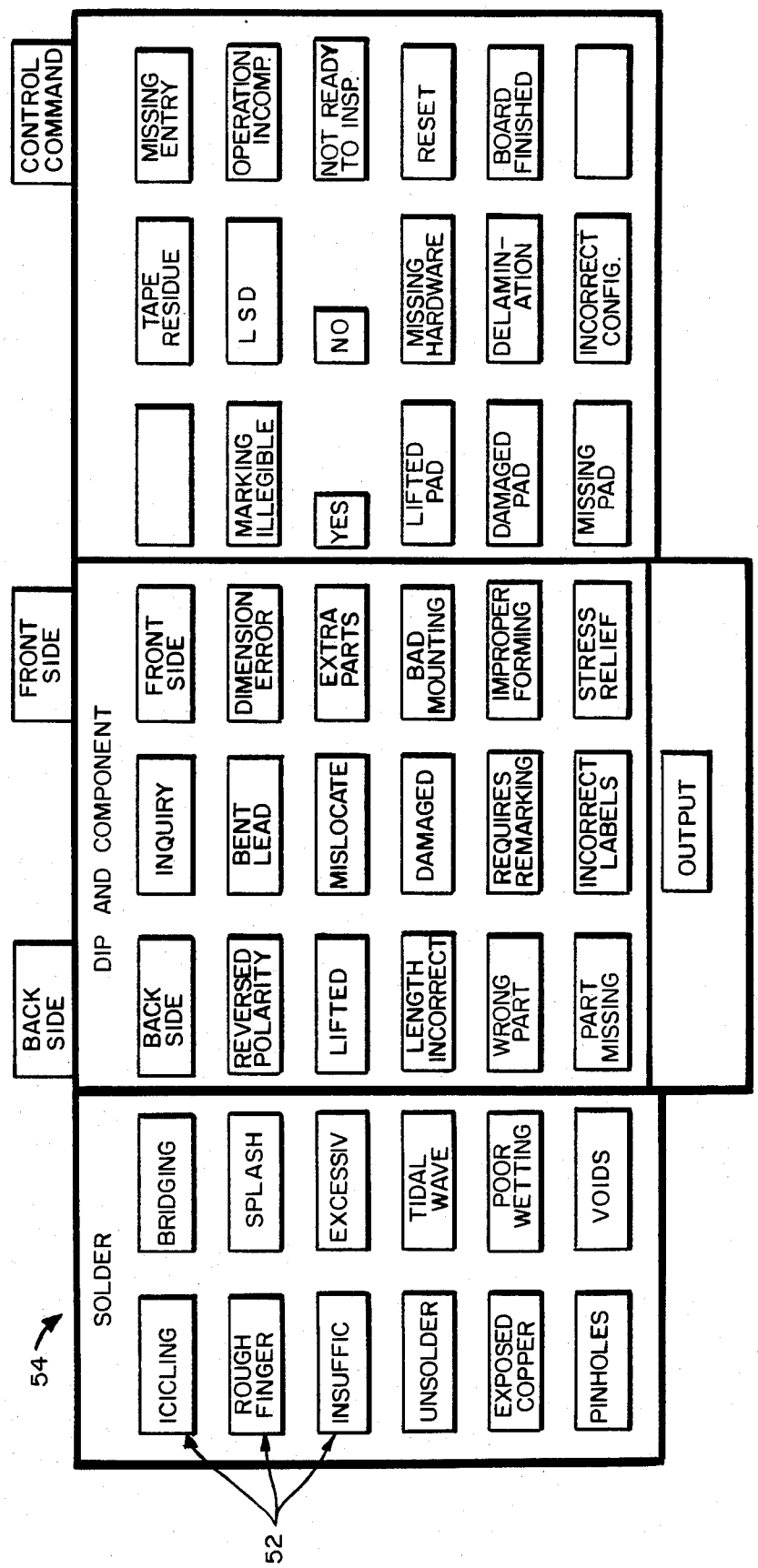
FIG. 3 is a view of an example data entry menu used on the inspection workstation of the present invention.

Next, the defect description is recorded by placing cursor 20 directly over one of fifty-eigth defect blocks 52 in a data entry menu 54 located in a data entry menu area 56, shown in FIGS. 1 and 3. Obviously, blocks 52 shown are only examples of blocks that could be used. Menu 54, as shown in FIG. 3, has blocks 52 generally associated with soldering, the dual-in-line package (DIP), other components, board conditions, and inspection commands.

The displayed data is accepted or rejected by actuating the cursor button over the "YES" block or "NO" block of menu 54.

If the displayed data is accepted, the information is transferred directly to computer 50 for further processing, storage and/or alarm actuation. If the displayed data is rejected, the information may be either corrected or discarded by the inspector.

After each defect is located and identified as that PWA 12, the next PWA 12 may be selected for inspection. If the PWA 12 is moved, the registration hole 18 must be relocated before any other defects are identified.

Referring to FIG. 4, microphones 36 output signals 38 to a translator 40 that converts signals 38 into digital signals 42 representing an x-position and y-position of reticle 22 at that instant. Digital signals 42 are input to a local controller 44 that outputs circuit information signals 46 to a readout 48 that displays such information as circuit reference, part number, etc. Also CRT display 58 can be used to display the above circuit information and in addition, colorgraphic techniques can be used to display the part being examined and the component under inspection. After each PWA 12 is completed, controller 44 sends information to computer 50 where data is stored, processed, and output for use in correcting deviations.

Figures 7, 8:
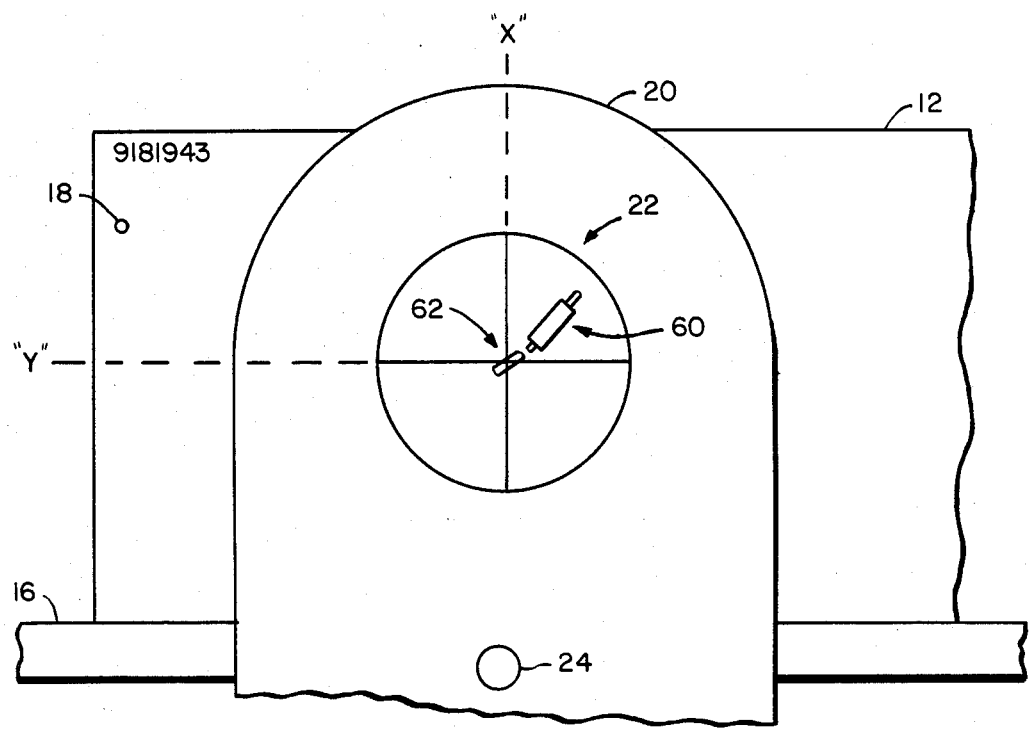
FIG. 7 is a partial view of FIG. 1.
FIG. 8 is a view of readout 48 of FIG. 1 with possible information therein.

FIG. 7 is a partial view of FIG. 1 which shows reticle 22, being the aiming device, centered on a target defect 62 being an open in a resistor 60 lead. Cursor 20 is positioned above PWA 12, shown only partially and only showing one electronic component therein. The PWA 12 identification information is shown above regristration hole 18. FIG. 8 illustrates, for example, readout 48, having information therein which reflects conditions in FIG. 7. A readout section 64 has a plurality of rows 66 of LEDs, for example, that display information. As shown therein, the inspector typed in PWA 12 identification number 9181943, for example; after registration of hole 18 and defect 62, controller 44 would output "RES" to be displayed in the "part type" row as well as the part number. This would be determined from information stored as to PWA 12 having the identification number given. The defect "DAMAGE" is selected by the inspector for the menu area 56 as to the component.

Some of the novel features of the method are as follows:

(1) The inspector can pick up PWA 12 to inspect it freely without loss of data because PWA 12 would be re-registered.
(2) PWA 12 is not held in position by any fixture thus facilitating movement from working area 60;
(3) Defect location is accurate to 0.020 inches with respect to an on-the-board reference point;
(4) Defect location amplifying information (circuit reference, part number, etc.) can be gained without using reference material, assembly drawing, part list, acceptable substitute part references, etc.;
(5) Defect description is automatically translated and displayed in testing machine usable codes, without reference tables, when entered;
(6) Inspector is free to request information from the local controller or host computer. Previous request consisted of manual search of assembly drawings, parts lists, control cards, and piece part drawings (often not the latest revision) for feedback;
(7) Post-recording handling errors inherent when documentation is processed is eliminated. Previously, method required manual recording into 4 different formats, key punch of data to computer load, and missed or duplicate entries of information; and
(8) There is immediate processing of documented defect data and therefore active control of process quality. Previous method required as much as one week processing time.

Figure 6:
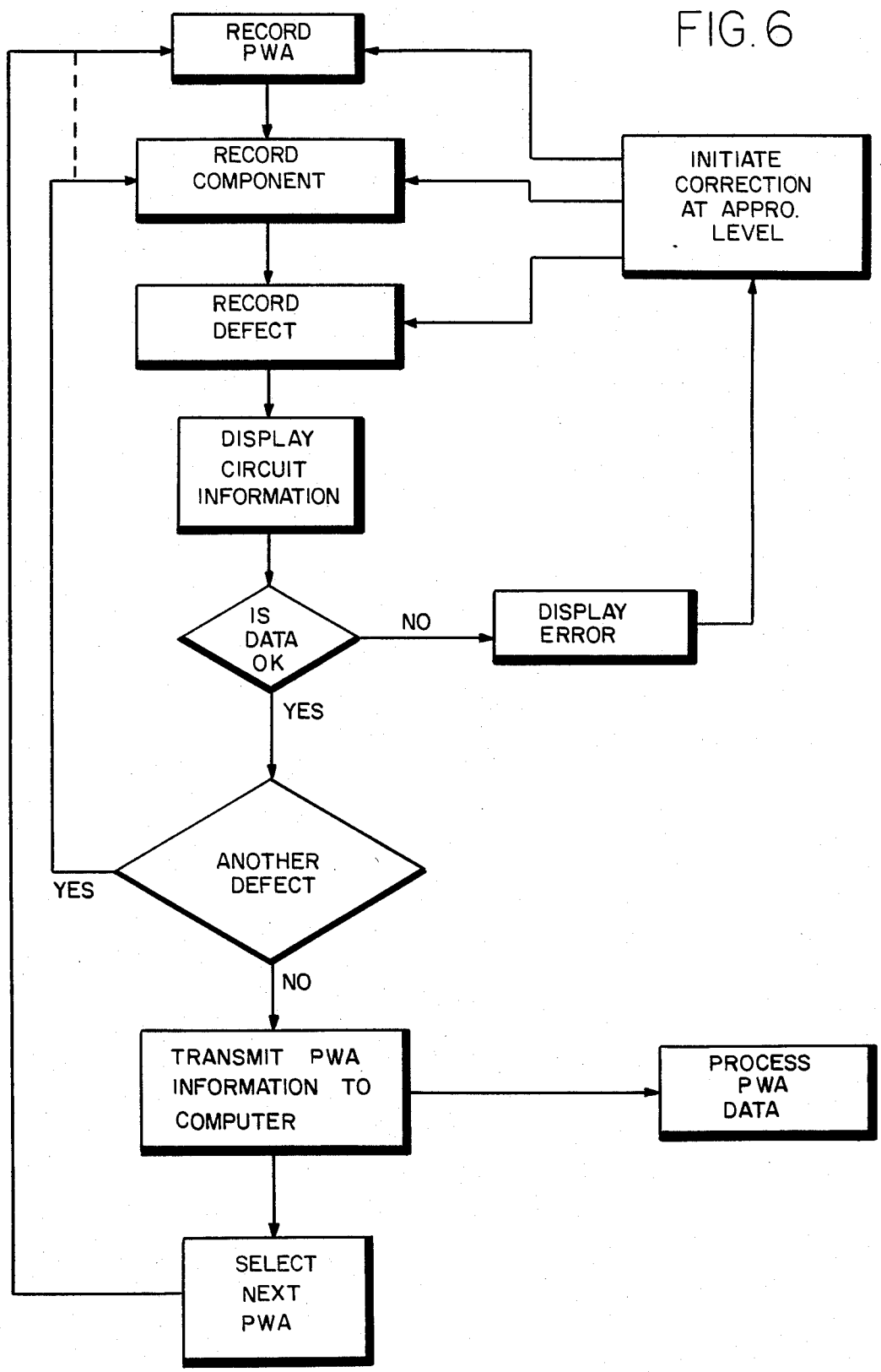
FIG. 6 is a logic flow diagram illustrative of the steps necessary in the programming of the general purpose computer used in the present invention.

FIG. 5 displays the steps the inspector follows to process each PWA 12. FIG. 6 displays the sequency of data handling, etc. used by controller 44 based upon the x-y coordinates input from translator 40.

In particular, referring to FIG. 5, the inspector must first identify each PWA 12 to controller 44 by either a keyboard input or a bar code scanner. This information may be directly attached to the PWA 12. The inspector then visually inspects the PWA 12 for defects. To enter this information into controller 44, the PWA 12 is then placed against reference bar 16. The x-y position of PWA 12 on bar 16 is determined when the inspector positions cursor 20 over hole 18 and depresses the actuator button 24. Next, the inspector moves the cursor 20 to a defect and again centers cursor 20 over the defect and depresses button 24. The type of defect is recorded next when the inspector selectively positions cursor 20 over menu 54 to select the type of defect such as "part missing" item. The inspector repeats these steps until the defects are recorded. When the inspection of PWA 12 is completed, the inspector selects "board finished" item in menu 54. This procedure is repeated for each PWA 12.

Referring to FIG. 6, the steps taken by controller 44, being essentially a dedicated computer, are closely associated with the actions, steps, taken by the inspector. For example, the controller 44 would have therein PWA 12 identify, the "component" identity, known by x-y information after PWA 12 is registered and the defect location is registered, and the defect "type" associated with the "component" type would also be known. This information would be compared to known data about each PWA 12. If the entered information was correct then the controller would indicate to the inspector that it is ready for another defect and/or PWA 12. If the entered information is incorrect in some manner then the inspector would be informed of the error. For example, the identity of the PWA 12 may be incorrect, no such component may exist on that PWA 12, registration is incorrect, etc. Correction of the error would be initiated. Inspector may be told to re-check. The production line may be notified of error. Once all the defect information is collected for each PWA 12, the data is sent to data processing. After this controller 44 would indicate that another PWA 12 is required for inspection.

Clearly, many modifications and variations of the present invention are possible in light of the above teachings and it is therefore understood, that within the inventive scope of the inventive concept, the invention may be practiced otherwise than specifically claimed.

What is claimed is:

1. An inspection workstation data entry method for inspecting an electronic assembly comprising the steps of:
   (a) determining whether a selected electronic assembly has at least one defect thereon by visual inspection;
   (b) entering identifying information of said selected electronic assembly having at least one defect thereon into a means for processing data;
   (c) positioning said electronic assembly against a reference bar in a work area of a workstation table, the position of said reference bar on said workstation table being known to said means for processing data;
   (d) positioning a sonic digitizer cursor over a registration point of said electronic assembly while said electronic assembly is positioned on said bar;
   (e) actuating said cursor while positioned over said registration point whereby a sound is emitted and received by a x-y linear microphone apparatus, said x-y linear microphone apparatus transmitting signals that correspond to the x-y location of said registration point;
   (f) positioning said cursor over a defect on said electronic assembly while on said bar;
   (g) actuating said cursor while positioned over said defect whereby a sound is emitted and received by said x-y linear microphone apparatus, said x-y linear microphone apparatus transmitting signals that correspond to the x-y location of said defect;
   (h) positioning said cursor over a defect description contained within a menu;
   (i) actuating said cursor while positioned over said defect description whereby a sound is emitted and received by said x-y linear microphone apparatus, said x-y linear microphone apparatus transmitting signals that correspond to the x-y location of said defect description;
   (j) reviewing information about said electronic assembly and said defect in said means for processing for correctness;
   (k) causing said information to be stored in said means for processing;
   (l) repeating steps (c) to (e) when said electronic assembly is repositioned against said bar;
   (m) repeating steps (f) to (k) for each defect on said electronic assembly; and
   (n) causing said information to be stored in a general purpose computer for data processing after all said defects upon said electronic assembly are recorded.

2. An inspection workstation data entry method as defined in claim 1 wherein said electronic assembly is a printed wiring assembly.

3. An inspection workstation for use in a data entry method, said workstation comprising:
   a table, said table having a substantially flat work area, said work area having a straight reference bar thereon, said bar acting as a stop against which an electronic assembly is placed during inspection;
   means for receiving a sound in an orthogonal manner, said means for receiving being mounted about said work area, said means for receiving outputting signals upon receipt of an omitted sound, said signals corresponding to an x-y position upon said work area;
   means for selectively emitting said sound, said means for emitting being hand transportable about said work area, said means for selectively emitting having aiming means, said aiming means positioning said means for selectively emitting said sound whereby when said emitted sound is received by said means for receiving, said output signals correspond to a position being a target of said aiming means;
   a data entry menu, said menu being located near said work area, said menu having a plurality of items, each item being a statement relating to the inspecting of said electronic assembly being inspected, an inspector selecting said statement by use of said means for selectively emitting sound;
   a display means, said display means being located near said table, said display means outputting information about said electronic assembly being inspected;

a data input means for inputting information; and a processing means, said processing means connected to said means for receiving, said display means, and said data input means, said processing means having stored therein the location of said reference bar, information about said electronic assembly, and a program to process defect information of said electronic assembly.

* * * * *